United States Patent [19]

Leising et al.

[11] Patent Number: 5,034,145
[45] Date of Patent: * Jul. 23, 1991

[54] PROCESS FOR THE PREPARATION OF MAGNETIZABLE MICROSPHERES BASED ON POLYSILOXANE AND THEIR BIOLOGICAL APPLICATION

[75] Inventors: Frederic Leising, Vernaison; Bernard Chauvel, Ermont; Ghislaine Torres, Lyon, all of France

[73] Assignee: Rhone-Poulenc Chimie, Courbevoie Cedex, France

[*] Notice: The portion of the term of this patent subsequent to Jan. 15, 2008 has been disclaimed.

[21] Appl. No.: 537,879

[22] Filed: Jun. 13, 1990

Related U.S. Application Data

[63] Continuation of Ser. No. 219,384, Jul. 15, 1988, abandoned.

[30] Foreign Application Priority Data

Jul. 15, 1987 [FR] France ............................. 87 09918

[51] Int. Cl.$^5$ ...................... H01F 1/26; C12N 11/02; C12N 11/14
[52] U.S. Cl. ................................. 252/62.54; 428/403; 428/405; 435/176; 435/180; 435/188
[58] Field of Search ....................... 252/62.53, 62.54; 428/403, 405; 435/176, 180, 188

[56] References Cited

U.S. PATENT DOCUMENTS

| | | | |
|---|---|---|---|
| 3,652,761 | 3/1972 | Weetall | 424/12 |
| 4,356,098 | 10/1982 | Chagnon | 252/62.53 |
| 4,695,392 | 9/1987 | Whitehead et al. | 252/62.54 |

OTHER PUBLICATIONS

Rhone-Poulenc Technical Bulletin, 3/3/87.

Primary Examiner—Gary P. Straub
Assistant Examiner—Stephen G. Kalinchak
Attorney, Agent, or Firm—Finnegan, Henderson, Farabow, Garrett and Dunner

[57] ABSTRACT

Magnetizable microspheres, optionally in aqueous dispersion, consisting of a matrix of at least one organopolysiloxane optionally bearing Si-vinyl groups or reactive and/or ionic units and magnetizable particles less than 300 angstroms in diameter encapsulated in the matrix. The magnetizable microspheres are prepared by homogenizing a solution of the organopolysiloxane and a magnetic fluid in the presence of water and a surfactant, removing the solvent for the organopolysiloxane and the carrier liquid of the magnetic fluid, and at least partially removing the water. The magnetizable microspheres are useful in biological applications as active supports.

12 Claims, No Drawings

PROCESS FOR THE PREPARATION OF MAGNETIZABLE MICROSPHERES BASED ON POLYSILOXANE AND THEIR BIOLOGICAL APPLICATION

This application is a continuation of application Ser. No. 07/219,384, filed July 15, 1988 now abandoned.

The present invention relates to magnetizable microspheres based on organopolysiloxane, to a process for preparation of such magnetizable microspheres and to their use in biological applications as active supports.

According to the invention, the magnetizable microspheres may be utilized alone or in aqueous dispersion and comprise:

a matrix based on at least one organopolysiloxane of the formula (I)

$$R''R'RSiO(SiR_2O)_n(SiRR''O)_mSiRR'R'' \qquad (I)$$

wherein:
the R radicals may be identical or different, and represent a $C_1$-$C_3$ alkyl, phenyl or 3,3,3-trifluoropropyl radical;
the R' radicals may be identical or different and may be an OH group or one of the radicals defined above for R;
the R'' radicals may be identical or different and may be one of the radicals defined above for R or may be a vinyl radical or a radical —R'''—X, where R''' is a divalent organic radical and X is a reactive and/or ionic group;
at least 50% of the R radicals are methyl radicals;
n and m are whole or fractional numbers having a value sufficient to provide a polymer having a viscosity of 20 to 10,000,000 mPas at 25° C., and preferably 400,000 to 10,000,000 mPas, and, if at least one R'' is selected from a vinyl radical or said —R'''—X radical, sufficient also to provide a ratio of the number of R units selected from a vinyl radical or said —R'''—X radical per organopolysiloxane molecule ranging from 1:1 to 1,000:1, and preferably ranging from 5:1 to 500:1;
and, encapsulated in the matrix, magnetizable particles having a diameter less than 300 angstroms, and preferably ranging from 80 to 120 angstroms.

Diorganosiloxy units not containing reactive or ionic groups within the scope of the present invention include, but are not limited to, the following:
$(CH_3)_2SiO$; $CH_3(CH_2=CH_2)$; $CH_3(C_2H_5)SiO$; $CH_3(C_6H_5)SiO$; $(C_6H_5)_2SiO$; $CF_3CH_2CH_2(CH_2)SiO$.

Blocking triorganosiloxy units within the scope of the present invention include, but are not limited to, the following:
$(CH_3)_3SiO_{0.5}$; $(CH_3)_2$—$CHSiO_{0.5}$; $(CH_3)_2C_6H_5SiO_{0.5}$; $CH_3(C_5H_5)SiO_{0.5}$; $CH_3(CH_2=CH)C_6H_5SiO_{0.5}$; $CH_2=CH(C_6H_5)SiO_{0.5}$; $(C_6H_5)SiO_{0.5}$.

Polyorganosiloxanes which are blocked with Si-OH or triorganosiloxy radicals but which do not contain reactive or ionic groups are well-known products; they may be prepared according to the processes described in French Patent Nos. 1,134,005, 1,198,749, 1,226,745, 978,058 and 1,025,150; all of which are specifically incorporated by reference herein.

Divalent organic radicals represented by the symbol R''' within the scope of the invention include, but are not limited to, the following: $C_1$-$C_{18}$ linear or branched alkylene radicals, optionally extended with 1 to 5 divalent ethylenamine groups, with 1 to 50 $C_1$-$C_3$ alkylene oxide groups or with a $$-O-CH_2-\underset{\underset{OH}{|}}{CH}-CH_2-$$

group, and polyoxyalkylene radicals containing 1 to 50 $C_1$-$C_3$ oxyalkylene units.

Examples of divalent radicals within the scope of the invention include, but are not limited to, the following:

$-CH_2-$; $+CH_2)_2$; $+CH_2)_3$; $-CH_2-\underset{\underset{CH_3}{|}}{CH}-CH_2$;

$+CH_2)_{10}$; $+CH_2)_{12}$; $+CH_2)_3NH-CH_2-CH_2-$;

$+CH_2)_3-OCH_2-$; $+CH_2)_3+OCH_2-CH_2)_{25}$;

$+CH_2)_3+O-CH_2-CH(CH_3)]_{15}$;

$+CH_2)_3OCH_2-\underset{\underset{OH}{|}}{CH}-CH_2-$

Reactive or ionic groups represented by X within the scope of the invention include, but are not limited to, the following: epoxy, hydroxy, carboxy, aldehyde, ester, aceto-ester, mercapto, mercapto ester, mercaptoalkoxy, amino, alkylamino, dialkylamino, trialkylamino, quaternary ammonium, amino alcohol, amido, hydrazide, hydrazino, $C_1$-$C_3$ haloalkyl, halobenzyl, cyano, cyanato,

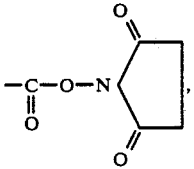

sulfate and sulfonyl.

The organopolysiloxanes of formula I bearing reactive or ionic groups are, for the most part, commercial products. They may be prepared according to well-known methods, for example:

by addition reaction of an organohydrogenopolysiloxane with an unsaturated compound $CH_2=CH-r-X$ wherein the group $CH_2=-r-$ corresponds to the divalent radical R''', by opening of the double bond (British Patent No. 2,138,185, U.S. Pat. No. 4,558,147, French Patent No. 2,447,942, all of which are specifically incorporated by reference herein);

by the condensation reaction of an organopolyhydroxysiloxane and an alkoxysilane or a hydrogenosilane bearing the group —R'' X (U.S. Pat. No. 4,476,188, specifically incorporated by reference herein), or with a ketene;

by a condensation reaction of an organohydrogenopolysiloxane and a hydroxy- or alkoxysiloxane bearing the group —R'' 'X;

by a nucleophilic substitution reaction such as that of an organoepoxysiloxane and an amine, or alcohol, a thiol, an acid, etc. (British Patent No. 2,138,845, specifically incorporated by reference herein).

The materials which can form the magnetizable particles encapsulated in the polyorganosiloxane matrix, include, but are not limited to, magnetite, maghemite, chromium dioxide, ferrites such as ferrites of manganese, nickel, manganese-zinc, etc., and alloys of cobalt, nickel, gadolinium, samarium-cobalt, etc. The preferred materials are magnetite and maghemite.

The quantity of magnetizable particles encapsulated in the polyorganosiloxane matrix preferably corresponds to approximately 0.5 to 50% by weight relative to the weight of the matrix, and more preferably ranges from 0.5 to 35% by weight.

The magnetizable microspheres of the present invention may be uniform in diameter or may be within a range of particle diameters; their diameter preferably ranges from 0.05 to 3 microns and more preferably ranges from 0.2 to 2 microns.

The magnetizable microspheres of the invention may be provided alone or as a dispersion in water. The quantity of magnetizable microspheres in the dispersed state in water preferably corresponds to approximately 10 to 70% by weight relative to the total weight of the dispersion, and more preferably ranges from 15 to 50% by weight. The present invention also relates to a process for preparing the magnetizable microspheres.

The process comprises:
introducing, into an aqueous medium containing a surfactant, a mixture of
a solution of at least one organopolysiloxane of formula I in an organic solvent having a boiling point less than 100° C., or capable of forming with water an azeotrope having a boiling point below 100° C., and preferably below 95° C.;
and a magnetic fluid consisting of magnetizable particles less than 300 angstroms in diameter, and preferably ranging from 80 to 120 angstroms, suspended in an organic carrier liquid which has a boiling point below 100° C. or is capable of forming with water an azeotrope having a boiling point below 100° C., and preferably below 95° C.; homogenizing the medium obtained; removing the organic solvent and the organic carrier liquid by distillation; and
optionally, at least partially removing the water.

Solvents for the polyorganosiloxane of formula I which can be employed include, but are not limited to, cyclohexane, methylene chloride, benzene, hexane, octane, toluene and carbon tetrachloride.

The solvent is employed to obtain a viscosity of the solution of less than 1,000 mPas at 25° C., and preferably less than 500 mPas. It will be understood by those skilled in the art that a solvent may not be necessary when the molecular weight of the organopolysiloxane is sufficiently low.

Magnetic fluids are commonly referred to in the art as "ferrofluids". They are extremely stable colloidal suspensions of ferro- or ferrimagnetic particles less than one micron in diameter, in a carrier liquid, and remain fluid in the presence of external magnetic fields.

The type of material that is capable of forming ferro- or ferrimagnetic particles has already been mentioned above. The preferred materials are magnetite and maghemite.

According to the invention, the carrier liquid can be any of those organic liquids which were mentioned as solvents for the polyorganosiloxane of formula I having a boiling point below 100° C. or capable of forming with water an azeotrope having a boiling point below 100° C. While being of the same type, the carrier liquid used for the magnetic fluid may be similar to or different from the solvent employed for the polyorganosiloxane.

The magnetic fluid may be prepared in a known manner, for example, according to the process described in U.S. Pat. No. 3,843,540, specifically incorporated by reference herein.

The preparation of the magnetic fluid involves a water-soluble dispersing agent which can be thermally decomposed to a form which is not water-soluble but is soluble in the organic liquid vehicle. On decomposing, the dispersing agent forms a non-water-soluble coating around each magnetizable particle. The preferred dispersing agents which are useful in this preparation include fatty acids, amines or amides which contain at least 12 carbon atoms, and the most preferred are fatty acids containing approximately 18 carbon atoms such as oleic, linoleic and linolenic acids.

The concentration of the magnetizable particles in the magnetic fluid preferably ranges from 20 to 60% by weight, and more preferably ranges from 30 to 60% by weight.

The quantity of magnetic fluid employed for carrying out the process of the invention is preferably such that the weight of magnetizable particles in the magnetic fluid corresponds to approximately 0.5 to 50% of the weight of polyorganosiloxane of formula I, and more preferably ranges from 0.5 to 35%.

The aqueous medium into which the mixture of polyorganosiloxane solution and magnetic fluid is introduced preferably has a concentration by weight of surfactant ranging from 0.5 to 15%, and more preferably ranges from 1 to 10%.

The surfactant present in the aqueous medium into which the mixture of organopolysiloxane solution and magnetic fluid is introduced can be any emulsifier of the nonionic, anionic or cationic type that is water-soluble or capable of forming micelles in water.

Nonionic surfactants that can be used in the invention include polyethoxylated fatty alcohols, polyethoxylated alkylphenols, polyethoxylated fatty acids, condensates of ethylene oxide and propylene oxide, polyethoxylated fatty amides polyethoxylated fatty amines, fatty acid esters, and ethanolamides.

Anionic surfactants that can be used in the invention include alkyl sulfates, alkylsulfonates, alkylarylsulfonates, sulfosuccinates and sodium sulfosuccinates.

Cationic surfactants that can be used in the invention include halides of fatty amines; halides, sulfates, methylsulfates and acetates of ethoxylated fatty amines; and $C_{10}$–$C_{18}$ quaternary ammonium halides.

The quantity of aqueous medium which can be employed is preferably such that the quantity of surfactant ranges from approximately 0.5 to 60% by weight, and more preferably ranges from 1 to 50% by weight, relative to the weight of the polyorganosiloxane of formula I.

The operation of introducing the polyorganosiloxane solution/magnetic fluid mixture into the aqueous medium is preferably carried out gradually with stirring at room temperature (15 to 40° C.).

The homogenization operation is preferably carried out in one or more stages at a temperature ranging from 20° to 60° C., using a vigorous agitation system such as a colloid mill, high pressure pump, vibratory agitator, ultrasonic apparatus, etc., until a dispersion of droplets of the organic phase containing the magnetizable particles is obtained. The droplets preferably range from approximately 0.065 to 3.2 microns, and more preferably range from 0.35 to 2.2 microns, in diameter. The droplets are comprised of the polyorganosiloxane of formula I, swollen with solvent(s) and containing the magnetizable particles.

The solvent or solvents for the polyorganosiloxane are then removed by distillation under vacuum.

An aqueous dispersion is thereby obtained of microspheres which preferably range in diameter from 0.05 to 3 microns, and more preferably from 0.2 to 2 microns, and which are comprised of a matrix based on the polyorganosiloxane of formula I and, encapsulated in the matrix, magnetizable particles preferably less than 300 angstroms in diameter, and more preferably ranging from 80 to 120 angstroms.

The weight of magnetizable microspheres in aqueous dispersion may be adjusted at will, either by the partial removal of the water after magnetization, or by the complete removal of the water after magnetization followed by addition of deionized water until a dry extract content preferably ranging from 10 to 70% by weight, and more preferably ranging from 15 to 50% by weight, is obtained.

If desired, the microspheres can be separated from the medium by simple magnetization.

The magnetizable microspheres of the present invention possess features which make them useful, in particular, in biological applications.

The magnetizable microspheres of the invention possess the following advantages:

they may be sterilized by heating for 2 hours at 122° C., and they remain active after sterilization;

the magnetizable particles which the microspheres contain are coated with a silicone matrix, thereby avoiding any interaction between the magnetizable particles and the reaction medium in which the microspheres are used;

they are biotolerant and non-toxic and therefore do not interfere with biological processes in vitro and can also be used in vivo; and they are magnetizable, which enables them to be separated by simple magnetization from the reaction medium in which they have been used, and as a result, washing operations also can be carried out more quickly.

The magnetizable microspheres of the invention may be used for example, as active supports:

for antibodies or antigens for diagnostic testing and for affinity separations of biological compounds; the binding of biological molecules can, if necessary, be carried out by well-known coupling methods, involving coupling agents (glutaraldehyde, water-soluble carbodimide), or which alternatively consist of activating the possible functional groups of polyorganosiloxane (for example, by diazotization, by the action of cyanogen bromide or hydrazine, etc.) and reacting the molecule to be bound;

for enzyme systems for biological reactions;

for the attachment of cell cultures;

for medicinal products or for tracer substances, for guiding these products or substances in vitro or in vivo to the chosen point of treatment;

for chemical molecules, permitting growth of these molecules by a rapid concatenation of particular reactions, as in peptide synthesis;

for chemical groups which are reaction catalysts; and for chemical groups for the separation or extraction of metals or optical isomers.

The examples which follow are intended to be used as a guide, and should not be considered to limit the scope and spirit of the invention.

The ferro fluids employed for carrying out the examples were prepared according to the following general procedure:

11 kg of $FeCl_3.6H_2O$ and then 7.5 kg of $FeSO_4.7H_2O$ were dissolved successively in 31 kg of water. The solution obtained was introduced into a reactor containing 20 kg of a 20% strength aqueous solution of ammonia. The reactor was brought to 60° C. and maintained at this temperature for 15 minutes; 2.4 kg of oleic acid were added and the medium was maintained with stirring at 60° C. for 15 minutes; the medium was cooled to 25° C. and then neutralized with 38% strength hydrochloric acid until a pH of 5.5 was obtained.

After vacuum filtration, the product was washed with water and then with acetone and dried. The product was taken up with an organic solvent (carrier liquid) and the residual water was then removed by azeotropic distillation.

The quantity of carrier liquid was such that the concentration of magnetite formed was 50% by weight.

The diameter of the magnetite particles, measured by electron microscopy, was of the order of 100 angstroms.

EXAMPLE 1

13 g of a ferrofluid in which the carrier liquid was cyclohexane (hence corresponding to 6.5 g of magnetite) were introduced into a solution consisting of 400 g of cyclohexane and 35 g of $\alpha,\omega$-dihydroxylated polydimethylsiloxane (prepared by the polycondensation of polydimethylsiloxanol oligomers) having the following characteristics:

$\overline{Mn} = 145,000 \quad \overline{Mw} = 312,000$
Viscosity: 1,500,000 mPas at 25° C.

The mixture obtained was homogenized in the presence of 800 g of water and 10 g of sodium dodecylbenzenesulfonate (corresponding to 28.5% by weight relative to the silicone oil) in an ultrasonic trough (SONIFIER B-30 apparatus marketed by BRANSON SONIC POWER CO.) until an average diameter of the dispersed microspheres of 0.8 micron was obtained.

The cyclohexane was then removed at 40° C. under reduced pressure (175 mbar). The final traces of cyclohexane were removed by azeotropic distillation with acetic acid; the residual cyclohexane content was less than 15 ppm (measured by gas chromatography).

A dispersion of microspheres whose average diameter was 0.65 micron (measurement performed in a COULTER NANOSIZER PSM series 17, marketed by Coulter Electronics Ltd.), and containing 18.5% by weight of magnetic particles of the order of 100 angstroms in diameter, was thereby obtained.

The microspheres were separated by magnetization and then redispersed in deionized water until a dry extract content of 47% was obtained.

EXAMPLE 2

Example 1 was repeated, cyclohexane being replaced by the same quantity of toluene, both as carrier liquid and as solvent for the polymer.

The average diameter of the magnetizable microspheres was 0.75 micron before removal of the toluene and 0.40 micron after removal of the final traces of toluene.

The content of magnetic particles in the microspheres was 18.5%

The aqueous dispersion was adjusted as in Example 1 to have a dry extract of 47%.

EXAMPLE 3

Example 1 was repeated, cyclohexane being replaced by the same quantity of methylene chloride, both as carrier liquid and as solvent for the polymer.

The average diameter of the magnetizable microspheres was 0.95 micron before removal of methylene chloride and 0.80 micron after removal of the traces of methylene chloride.

The content of magnetic particles in the microspheres was 18.5%.

The aqueous dispersion was adjusted according to the method of Example 1 to obtain a dry extract of 30%.

EXAMPLE 4

The operation described in Example 1 was repeated using a MANTON-GAULIN (marketed by the company Manton-Gaulin) as a homogenizer.

Under a pressure of 450 kg/cm$^2$ and after a first run, an average particle diameter of the dispersion of 0.80 micron was obtained; after a second run, the average particle diameter was 0.65 micron.

The average diameter of the magnetizable microspheres after removal of the cyclohexane was 0.5 micron; the content of magnetic particles in the microspheres was 18.5% by weight.

The aqueous dispersion was adjusted according to the method of Example 1 to obtain a dry extract of 20%.

EXAMPLE 5

The operation described in Example 1 was repeated using a SUPRATON (marketed by KRUPP TECHNIQUES INDUSTRIELLES) as a homogenizer.

After one run, an average particle diameter of the dispersion of the order of 1 micron was obtained.

After removal of the cyclohexane, the average diameter of the magnetizable microspheres was 0.9 micron; the content of magnetic particles in the microspheres was 18.5% by weight.

The aqueous dispersion was adjusted according to the method of Example 1 to obtain a dry extract of 15%.

EXAMPLE 6

The operation described in Example 1 was repeated, using an ULTRA TURREX IKA WERK (marketed by Prolabo) as a homogenizer. The average particle diameter of the dispersion was of the order of 1.4 microns before removal of the cyclohexane; after removal of the cyclohexane, the average diameter of the magnetizable microspheres was 1.2 microns; the content of magnetizable particles was 18.5% by weight.

EXAMPLE 7

15 g of ferrofluid, in which the carrier liquid was cyclohexane (corresponding to 7.5 g of magnetite) were introduced into a solution consisting of 400 g of cyclohexane and 75 g of α,ω-dihydroxylated polydimethylsiloxane having the following characteristics:

$\overline{Mn}$: 179,000   $\overline{Mw}$ = 535,000
Viscosity: 6,500,000 mPas at 25° C.

The mixture obtained was homogenized in the presence of 800 g of water and 23.5 g (corresponding to 31% by weight relative to the polymer) of CEMULSOL ON 10-20 [mixture of ethoxylated octylphenol and ethoxylated nonylphenol, marketed by the Societe Francaise d. Organo-Synthese (French Organic Synthesis Company)] in an ultrasonic trough (SONIFIER B 30 apparatus). After 5 minutes of homogenization, a dispersion of magnetizable microspheres possessing an average particle diameter of 0.95 micron was obtained. After removal of the cyclohexane, the average particle diameter was 0.8 micron.

The microspheres contained 10% by weight of magnetizable particles of the order of 100 angstroms in diameter.

The aqueous dispersion was adjusted according to the method of Example 1 to obtain a dry extract of 15%.

EXAMPLE 8

20 g of a ferrofluid in which the carrier liquid was cyclohexane (corresponding to 10 g of magnetite) were introduced into a solution consisting of 185 g of methylene chloride and 20 g of an α,ω-dihydroxylated polydimethylsiloxane having the following characteristics:

$\overline{Mn}$ = 145,000   $\overline{Mw}$ = 312,000
Viscosity: 1,500,000 mPas at 25° C.

The mixture obtained was homogenized in the presence of 800 g of water and 10 g of sodium lauryl sulfate, corresponding to 50% by weight relative to the polymer, in an ultrasonic trough (SONIFIER B 30 apparatus). After 5 minutes of homogenization, a dispersion of magnetizable microspheres possessing an average particle diameter of 0.80 micron was obtained.

After removal of the methylene chloride, the average particle diameter was 0.7 micron.

The microspheres contained 50% by weight of magnetizable particles of the order of 100 angstroms in diameter.

The aqueous dispersion was adjusted according to the method of Example 1 to obtain a dry extract of 20%.

EXAMPLE 9

20 g of a ferrofluid in which the carrier liquid was toluene (corresponding to 10 g of magnetite) were introduced into a solution consisting of 500 g of toluene and 50 g of an α,ω-dihydroxylated polydimethylsiloxane having the following characteristics:

$\overline{Mn}$ = 96,000   $\overline{Mw}$ = 205,000
Viscosity: 2,500,000 mPas at 25° C.

The mixture obtained was homogenized in the presence of 800 g of water and 3.5 g of sodium dodecylbenzenesulfonate in an ultrasonic trough (SONIFIER B 30). After 30 minutes of homogenization, a dispersion of magnetizable microspheres possessing an average particle diameter of 0.55 micron was obtained. After removal of the toluene, the average particle diameter was 0.45 micron.

The microspheres contained 20% by weight of magnetizable particles of the order of 100 angstroms in diameter.

The aqueous dispersion was adjusted according to the method of Example 1 to obtain a dry extract of 20%.

EXAMPLE 10

20 g of a ferrofluid in which the carrier liquid was toluene (corresponding to 10 g of magnetite) were introduced into a solution consisting of 200 g of toluene and 20 g of an ethylenically unsaturated polyorganosiloxane obtained by the polycondensation of polydimethylsiloxanol oligomers in the presence of 10% by weight of tetramethyltetravinyl-cyclotetrasiloxane oligomers, the characteristics of this polymer being as follows:

$\overline{Mn}$ = 114,000    $\overline{Mw}$ = 222,000
Viscosity: 400,000 mPas at 25° C.
Si-vinyl content: 650 units per chain The mixture obtained was homogenized in the presence of 200 g of water and 2 g of sodium dodecylbenzenesulfonate in an ultrasonic trough (SONIFIER B 30). After 10 minutes of homogenization, a dispersion of magnetizable microspheres possessing an average particle diameter of 0.75 micron was obtained. After removal of the toluene, the average particle diameter was 0.5 micron.

The aqueous dispersion was adjusted according to the method of Example 1 to obtain a dry extract of 20%.

The microspheres contained 50% by weight of magnetizable particles of the order of 100 angstroms in diameter.

EXAMPLE 11

The operation described in Example 10 was repeated, toluene being replaced by cyclohexane as carrier liquid of the ferrofluid and as solvent for the polyorganosiloxane, the 20 g of polyorganosiloxane of Example 10 being replaced by 20 g of a polyorganosiloxane, also ethylenically unsaturated, obtained by the polycondensation of polydimethylsiloxanol oligomers in the presence of 5% by weight (instead of 10%) of tetramethyltetravinylcyclotetrasiloxane oligomers, the characteristics of which are as follows:

$\overline{Mn}$ = 48,500    $\overline{Mw}$ = 110,000
Viscosity: 9,500,000 mPas at 25° C.
Si-vinyl content: 140 units per chain The average particle diameter of the magnetizable microspheres was 0.8 micron before removal of the cyclohexane and 0.6 micron after removal of the cyclohexane.

The aqueous dispersion was adjusted according to the method of Example 1 to obtain a dry extract of 13%.

The microspheres contained 50% by weight of magnetizable particles of the order of 100 angstroms in diameter.

EXAMPLE 12

20 g of a ferrofluid in which the carrier liquid was cyclohexane (corresponding to 10 g of magnetite) were introduced into a solution consisting of 400 g of cyclohexane and a mixture of the following polymers:

50 g of the α,ω-hydroxylated polydimethylsiloxane of Example 7
($\overline{Mn}$=179,000, $\overline{Mw}$=535,000); and 5 g of an epoxidized polydimethylsiloxane oil of the formula

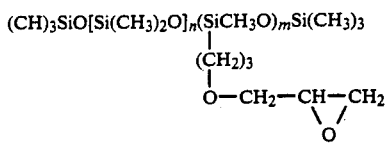

the characteristics of which are as follows:
$\overline{Mn}$ = 5,000
Concentration of epoxide groups: 174 meq/100 g of oil (equivalent to 8 units per chain of epoxidized oil).

The viscosity of the combination of polyorganosiloxanes was 6,000,000 mPas at 25° C.

The mixture obtained was homogenized in the presence of 800 g of water and 5.5 g of CEMULSOL ON 10-20 in an ultrasonic trough (SONIFIER B 30). After 10 minutes of homogenization, a dispersion of magnetizable microspheres possessing epoxy groups at their periphery was obtained. These microspheres possess an average particle diameter of 0.95 micron. After removal of the cyclohexane, this diameter was 0.8 micron.

The microspheres contained 18% by weight of magnetizable particles of the order of 100 angstroms in diameter.

The aqueous dispersion was adjusted according to the method of Example 1 to obtain a dry extract of 36%.

EXAMPLE 13

8 g of a ferrofluid in which the carrier liquid was cyclohexane (corresponding to 4 g of magnetite) were introduced into a solution consisting of 400 g of cyclohexane and a mixture of the following polymers:
25 g of the α,ω,-hydroxylated polydimethyl-siloxane of Example 7
($\overline{Mn}$=179,000, $\overline{Mw}$=535,000); and
2 g of a polydimethylsiloxane oil having a formula similar to that of the epoxidized oil of Example 12, but possessing the following characteristics:
$\overline{Mn}$=1,250
Concentration of epoxide groups: 498 meq/100 g of oil (equivalent to 15 epoxide units per chain of epoxidized oil).

The viscosity of the combination of polyorganosiloxanes is 6,000,000 mPas at 25° C.

The mixture obtained was then treated as in Example 12.

The average particle diameter of the magnetizable microspheres was 0.8 micron before removal of the cyclohexane and 0.7 micron after removal of the cyclohexane.

The microspheres contained 13.3% by weight of magnetizable particles of the order of 100 angstroms in diameter.

The aqueous dispersion was adjusted according to the method of Example 1 so as to obtain a dry extract of 36%.

EXAMPLE 14

The operation of Example 13 was repeated, the 2 g of polydimethylpolysiloxane oil of $\overline{Mn}$=1,250 and possessing a concentration of epoxide groups of 498 meq/100 g of oil being replaced by 2 g of a polydimethylpolysiloxane oil of similar formula, of $\overline{Mn}=1,250$ and possessing a concentration of epoxide groups of 390 meq/100 g of oil (equivalent to 9 epoxide units per chain of epoxidized oil).

The viscosity of the combination of polyorganosilanes was 6,000,000 mPas at 25° C.

The average particle diameter of the magnetizable microspheres was 0.9 micron before removal of the cyclohexane and 0.8 micron after removal of the cyclohexane.

The microspheres contained 13.3% by weight of magnetizable particles of the order of 100 angstroms in diameter.

The aqueous dispersion was adjusted according to the method of Example 1 to obtain a dry extract of 15%.

We claim:

1. Magnetizable microspheres, comprising a matrix based on at least one organopolysiloxane of the formula (I)

$$R''R'RSiO(SiR_2O)_n(SiRR''O)_mSiRR'R'' \qquad (I)$$

wherein:
the R radicals may be identical or different, and are selected from a $C_1-C_3$ alkyl radical and a phenyl radical;
the R' radicals may be identical or different and are selected from an OH group, a $C_1-C_3$ alkyl radical and a phenyl radical;
the R'' radicals may be identical or different and are selected from a $C_1-C_4$ alkyl radical, a phenyl radical, 3,3,3-trifluoropropyl, a vinyl radical and a radical —R'''—'X wherein R''' is a divalent organic radical and X is selected from an epoxy, hydroxy, carboxy, aldehyde, ester, aceto-ester, mercapto, mercapto ester, mercaptoalkoxy, amino, alkylamino, dialkylamino, trialkylamino, quaternary ammonium, amino alcohol, amido, hydrazide, hydrazino, C1–C3 haloalkyl, cyano, cyanato,

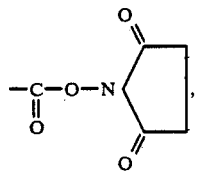

sulfate, sulfonyl and halobenzyl group,
at least 50% of the R radical are methyl radicals;
n and m are whole or fractional numbers having a value sufficient to provide a matrix having a viscosity ranging from 400,000 to 10,000,000 mPas at 25° C., and, if at least one R'' is selected from a vinyl radical or said —R'''—'X radical, n and m have values sufficient to provide a ratio of the number of R'' units selected from a vinyl radical or said —R'''—X radical per organopolysiloxane molecule ranging from 1:1 to 1,000:1;
and, encapsulated in said matrix, magnetizable particles having a diameter less than 300 angstroms.

2. The magnetizable microspheres as claimed in claim 1, wherein the divalent radical R''' is selected from a $C_1-C_{18}$ linear alkylene radical, a $C_1-C_{18}$ branched alkylene radical and a polyoxyalkylene radical containing from 1 to 50 $C_1-C_3$ oxyalkylene units.

3. The magnetizable microspheres as claimed in claim 2, wherein at least one of said $C_1-C_{18}$ linear alkylene radical and said $C_1-C_{18}$ branched alkylene radical is extended with groups selected from among 1 to 5 ethylenamine divalent groups, 1 to 50 $C_1-C_3$ alkylene oxide divalent groups and a $$-O-CH_2-\underset{\underset{OH}{|}}{CH}-CH_2-$$

group.

4. The magnetizable microspheres as claimed in claim 1, wherein the magnetizable particles are selected from magnetite, maghemite, chromium dioxide, ferrites and alloys of cobalt, nickel, gadolinium and samarium-cobalt.

5. The magnetizable microsphere as claimed in claim 1, wherein said ferrites are selected from ferrites of manganese, nickel and manganese-zinc.

6. The magnetizable microspheres as claimed in claim 5, wherein said magnetizable particles are magnetite.

7. The magnetizable microspheres as claimed in claim 1, wherein the diameter of said microspheres ranges from 0.05 to 3.

8. The magnetizable microspheres as claimed in claim 1, wherein said microspheres contain from 0.5 to 50% by weight of magnetizable particles relative to the matrix.

9. An aqueous dispersion of the magnetizable microspheres of claim 1, comprising 10 to 70% magnetizable microspheres by 10. The microspheres of claim 1, wherein at least one R radical is a 3,3,3-trifluoropropyl radical.

11. The microspheres of claim 1, wherein at least one R' radical is a 3,3,3-trifluoropropyl radical.

12. The microspheres of claim 1, wherein at least one R'' radical is a 3,3,3-trifluoropropyl radical.

* * * * *